United States Patent [19]

Lindstrom

[11] E Re. 30,059

[45] Reissued Jul. 31, 1979

[54] ASSAY FOR MYASTHENIA GRAVIS

[75] Inventor: Jon M. Lindstrom, Del Mar, Calif.

[73] Assignee: The Salk Institute for Biological Studies, San Diego, Calif.

[21] Appl. No.: 888,691

[22] Filed: Mar. 20, 1978

Related U.S. Patent Documents

Reissue of:

[64] Patent No.: 4,033,722
Issued: Jul. 5, 1977
Appl. No.: 603,243
Filed: Aug. 8, 1975

[51] Int. Cl.[2] ..... G01N 33/16; A61K 43/00

[52] U.S. Cl. ..... 23/230.3; 23/230 B; 23/920; 424/1; 424/1.5; 424/12

[58] Field of Search ..... 23/230 B, 920, 230.3; 424/1, 1.5, 12

[56] References Cited

PUBLICATIONS

Fambrough et al., "Neuromuscular Junction in Myasthenia Gravis Decreased Acetylcholine Receptors," Science, vol. 182, Oct. 1973, pp. 293-295.

Almon et al., "Serum Globulin in Myasthenia Gravis: Inhibition of $\alpha$-Bungarotoxin Binding to Acetylcholine Receptors," Science, vol. 186, No. 4158, Oct. 1974, pp. 55-57.

Skelley et al., "Radioimmunoassay," Clinical Chemistry, vol. 19, No. 2, (1973), pp. 146, and 161-163.

*Primary Examiner*—Arnold Turk
*Attorney, Agent, or Firm*—Fitch, Even & Tabin

[57] ABSTRACT

A serum assay system for diagnosis of myasthenia gravis. The assay system includes a complex of acetylcholine receptor protein and a toxin labeled with a radioactive isotope. The complex is incubated with a serum sample from a patient. During incubation, antibodies engendered by myasthenia gravis bind to receptor sites in the complex. The resulting complex containing the antibodies is precipitated by addition of anti-immunoglobulin. Radioactivity in the resulting precipitate is measured and compared with a control.

8 Claims, No Drawings

ASSAY FOR MYASTHENIA GRAVIS

Matter enclosed in heavy brackets [ ] appears in the original patent but forms no part of this reissue specification; matter printed in italics indicates the additions made by reissue.

The present invention relates generally to a biochemical assay system for use in medical diagnosis. More particularly, the present invention relates to a bio-assay for myasthenia gravis and to the diagnosis of myasthenia gravis in humans.

Myasthenia gravis is a disease characterized by muscular weakness which particularly affects the muscles of the face, tongue and neck. Myasthenia gravis is commonly mistaken for other pathological and neurological disorders. Electromyogram response to repeated electrical nerve stimulation has been the best available diagnostic test for myasthenia gravis. However, electromyogram testing is not wholly satisfactory since this technique must be performed and evaluated by a specialized neurologist, and the effects observed are small. It would be desirable to provide a more reliable diagnostic test for determination of myasthenia gravis and one that would be accessible to any physician simply by assay of a sample of the patients serum in a clinical laboratory. Also, it would be especially desirable to have an easy method to assay patients response to immunosuppressive therapy.

Accordingly, it is a principal object of the present invention to provide a serum-assay system for diagnosis of myasthenia gravis. It is another object of the invention to provide a diagnostic method for determination of myasthenia gravis which is highly selective and which can distinguish myasthenia gravis from other diseases.

Generally, in accordance with various features of the present invention a complex of acetylcholine receptor protein (AChR) and a toxin labeled with a radioactive isotope is prepared. The complex is incubated with a serum sample from a patient. During incubation, anitbodies engendered by myasthenia gravis bind to AChR in the complex. The resulting complexes of anti-body-AChR-$I^{125}$-toxin are precipitated along with carrier immunoglobulin by addition of anti-immunoglobulin. Radioactivity in the resulting precipitate is measured and is compared with a control. The radioactivity measurement can be converted to a titer expressed as moles of the AChR binding sites for toxin which are bound by the antibody per liter.

Acetylcholine receptor protein (AChR) is extracted from mammalian muscle tissue. Preferably, the AChR is extracted from human muscle tissue, since non-human muscle tissue AChR provides a less effective antigen for human antibody. One volume of minced muscle tissue is homogenized in a high shear blendor at 4° C. in 4 volumes of an aqueous salt solution. The aqueous salt solution is 0.1 M NaCl, 0.01 M $NaPO_4$ (pH 7.0), and 0.01 M $NaN_3$. The homogenized muscle tissue is then centrifuged for 30 minutes at $10^5 \times g$. The pellet resulting from the centrifugal separation is extracted with 2 volumes of the above described salt solution containing 2 percent by weight of a surfactant. A surfactant available under the tradename Triton X-100 from *the* Sigma Company is preferred. The extraction is effected by shaking the residue for 1 hour in the solution. After extraction, the mixture is centrifuged for 1 hour at $10^5 \times g$. The supernate from the centrifugation contains AChR at a level of 2 to $8 \times 10^{-10}$ M.

The toxin used in the complex may be any of the known toxins which bind to AChR. Such toxins are derived from cobras or sea snakes. Naja naja siamensis toxin and $\alpha$ bungarotoxin from Bungarus multicinctus have been found to be particularly effective and are preferred.

Purified toxin is labeled with any suitable radioactive isotope in accordance with standard procedures. $I^{125}$ is preferred for reasons of cost and availability. The toxin is labeled with $I^{125}$ according to standard techniques using chloramine T as follows: To 5 mci of carrier-free $I^{125}$ ($2.4 \times 10^{-9}$ moles) is added 10 microliters of 0.1 M $NaPO_4$ buffer (pH 7.0) followed by sufficient 0.1 M HCl to neutralize the NaOH in which the $I^{125}$ is shipped. Toxin ($2.4 \times 10^{-8}$ moles) and NaI ($2.4 \times 10^{-8}$ moles) are added in 40–50 microliters of 0.1 M $NaPO_4$ (pH 7.0) to the neutralized $I^{125}$. Chloramine T is added (10 microliters containing $2.8 \times 10^{-8}$ moles) and the solution is agitated for 10 minutes. The solution along with 100 microliters of buffer is applied to a Sephadex G 25 column ($1 \times 10$ cm). A complex of $I^{125}$-toxin elutes in the void volume along with 86 percent of the radioactivity. When the above procedure is repeated but NaI is omitted and the chloramine T is reduced to $0.93 \times 10^{-8}$ moles, the incorporation of $I^{125}$ is 100 percent. Both methods produce a complex of $I^{125}$-toxin effective to label AChR.

AChR is complexed with the $I^{125}$-toxin by incubation with excess $I^{125}$-toxin for several hours. The $I^{125}$-toxin bound to AChR is measured by using a Sephadex G-200 column (10 cm $\times$ 1 cm) which separates $I^{125}$-toxin-AChR complexes from free $I^{125}$-toxin. Since AChR is present as a minor component of the muscle extract, it is highly specific labeling of AChR by $I^{125}$-toxin that gives the specific antigen used in this assay.

The concentration of serum antibodies from a blood sample of a patient which couple to the AChR complex is measured by a double precipitin assay. AChR complexed with $I^{125}$-toxin from either Naja naja siamensis or Bungarus multicinctus is incubated with diluted serum. Antibodies found in sera of patients with myasthenia gravis are attached to AChR during the incubation. The resulting complex of antibody-AChR-$I^{125}$-toxin is precipitated along with other immunoglobulin in the serum by addition of anti-immunoglobulin. Radioactivity in the resulting precipitate is then measured. Radioactivity in a precipitate obtained by omitting AChR from the reaction mixture is subtracted from this value to correct for radioactivity nonspecifically trapped in the pellet. Using the known specific radioactivity of $I^{125}$-toxin the corrected value for radioactivity in the pellet is converted to a titer expressed in moles of toxin binding sites bound per liter of serum. Virtually all patients having myasthenia gravis which were tested had high titers, whereas patients which did not have myasthenia gravis had low or no titers.

In a specific example of the present invention, the antibody-AChR titer of various human subjects known to be suffering from several neurological diseases was determined. Human AChR was extracted from human muscle tissue in accordance with the method described hereinabove. $I^{125}$-toxin was prepared in accordance with the method described above. Triplicate 1 ml aliquots of human AChR ($5 \times 10^{-10}$ M) were labeled in the presence of $I^{125}$-toxin ($1 \times 10^{-9}$ M) by incubation at 4° C. for 4 hours. Triplicate 1 ml aliquots of $I^{125}$-toxin ($1\times10^{-9}$ M, Naja naja siamensis) were also prepared to serve as a control. 5 microliters of serum obtained from the blood of the patient were added to each tube. After overnight incubation at 4° C., goat anti-human gamma-globulin (15 percent $Na_2SO_4$ cut) was added. The amount of goat serum used was that which gave a maximum precipitate when tested with 5 microliters of normal human serum (usually about 15 microliters). After 4 hours incubation at 4° C. the tubes were centrifuged, the pellet was washed once and the radioactivity of the pellet determined. The radioactivity of the $I^{125}$-toxin blanks was subtracted from the average value for the tubes containing AChR. The titer in terms of the average moles of the toxin binding sites which were bound by antibodies per liter was determined in accordance with the following formula:

$$\frac{(\text{cpm/assay pellet}) \times \dfrac{10^5 \text{ microliters/liter}}{(5 \text{ microliters serum/assay}}}{\text{cpm/mole toxin} - I^{125}} = \frac{\text{moles toxin binding sites bound}}{\text{liter serum}}$$

where: Cpm = counts of radioactivity per minute. The results for the several nuerologic diseases investigated are set forth below in Table I.

TABLE I

Anti-Human Muscle AChR Antibody Titer in Several Neurologic Diseases

| Diagnosis | Number of Subjects | Anti-AChR Titer (Average moles toxin binding sites bound/liter $\times 10-^{-10}$) |
|---|---|---|
| Myasthenia Gravis | 50 | 85.0 |
| Control (no neurologic disease) | 35 | 0.26 |
| Myasthenia Syndrome (Eaton-Lambert Syndrome) | 4 | 0.36 |
| Polymyositis | 6 | 0.32 |
| Duchenne Muscular Dystrophy | 6 | 0.29 |
| Myotonic Dystrophy | 5 | 0 |
| Becker Dystrophy | 4 | 0.39 |
| Fascioscapulohumeral Dystrophy | 2 | 0.90 |
| Limb-Girdle Syndrome | 6 | 0.27 |
| Charcot-Marie-Tooth Syndrome | 1 | 0.09 |
| Anterior Horn Cell Disease | 1 | 0.50 |
| Werdnig Hoffmann | 1 | 0.70 |
| McArdle's Syndrome | 1 | 0 |
| Kugelberg-Welander Syndrome | 1 | 0.37 |
| Multiple Sclerosis | 6 | 0 |

It has been determined that the severity of myasthenia gravis in the subject is not always directly related to the titer as determined by the method of the invention. However, the titer is higher, on the average, for those patients which are more severely afflicted with myasthenia gravis. Fifty-three patients suffering from myasthenia gravis at various levels of severity were assayed in accordance with the bio-assay system of the invention. The results are set forth in Table II.

TABLE II

Severity of Myasthenia Gravis and Anti-AChR Antibody Titer of Serum

| Intensity of M.G. (by Modified Osserman criteria) | Number of Patients | Titer $\times 10^{-10}$ Range | Average |
|---|---|---|---|
| Remission | 4 | .03-.75 | .39 |
| Ocular | 5 | 2.0-50.0 | 14.1 |
| Mild generalized | 21 | 0-300.0 | 77.3 |
| Moderately severe | 21 | .88-297.0 | 81.1 |
| Acute severe | 1 | | 250.0 |
| Late severe | 1 | | 16.0 |

It can be seen that the bio-assay system of the invention provides a positive diagnostic test for the determination of myasthenia gravis in humans. If the titer of a serum sample from the patient is above $2.0\times10^{-10}$ moles of toxin binding cites bound per liter, the patient can be positively identified as having myasthenia gravis and can be treated in accordance with known methods. If a serum sample from the patient has a titer in the range of 1.0 to $2.0\times10^{-10}$, myasthenia gravis can be suspected. If the titer falls below $1.0\times10^{-10}$, tests for other neurological diseases are then made on the patient.

What is claimed is:

1. A biochemical assay system comprising a complex of acetylcholine receptor protein derived from [human] *mammalian* muscle with toxin labeled with a radioactive isotope.

2. A biochemical assay system in accordance with claim 1 wherein said toxin is derived from cobras and sea snakes.

3. A biochemical assay system in accordance with claim 1 wherein said toxin is from Naja naja siamensis or Bungarus multicinctus.

4. A biochemical assay *system* in accordance with claim 1 wherein said radioactive isotope is $I^{125}$.

5. A diagnostic test for determination of myasthenia gravis comprising the steps of preparing a complex of acetylcholine receptor protein derived from [human] *mammalian* muscle, toxin and a radioactive isotope, incubating said complex with a serum sample from a patient so as to join antibodies engendered by myasthenia gravis to receptor in said complex, precipitating said antibody-complex with anti-immunoglobulin and measuring the radioactivity of said precipitate.

6. A diagnostic test in accordance with claim 5 wherein said toxins are derived from cobras and sea snakes.

7. A diagnostic test in accordance with claim 5 wherein said toxin is from Naja naja siamensis or Bungarus multicinctus.

8. A diagnostic test in accordance with claim 5 wherein said radioactive isotope is $I^{125}$.

* * * * *

UNITED STATES PATENT AND TRADEMARK OFFICE

CERTIFICATE OF CORRECTION

PATENT NO. : Re. 30,059

DATED : July 31, 1979

INVENTOR(S) : Jon M. Lindstrom

It is certified that error appears in the above-identified patent and that said Letters Patent are hereby corrected as shown below:

In column 2, line 61, "neurological" should be --neurologic--.

In column 3, line 17, "$10^5$" should be --$10^6$--.

Signed and Sealed this

*Twenty-second* Day of *January 1980*

[SEAL]

*Attest:*

SIDNEY A. DIAMOND

*Attesting Officer*

*Commissioner of Patents and Trademarks*